United States Patent [19]

Bulten et al.

[11] Patent Number: 4,501,702

[45] Date of Patent: Feb. 26, 1985

[54] GERMANIUM COMPOUNDS

[75] Inventors: Eric J. Bulten, Blaricum; Antonius M. J. Liebregts, Nieuwegein, both of Netherlands

[73] Assignee: Nederlandse Centrale Organisatie voor Toegepast-Natuurwetenschappelijk Onderzoek, The Hague, Netherlands

[21] Appl. No.: 268,139

[22] Filed: May 29, 1981

[30] Foreign Application Priority Data

May 30, 1980 [NL] Netherlands ......................... 8003159
May 8, 1981 [NL] Netherlands ......................... 8102268

[51] Int. Cl.$^3$ .............................................. C07F 7/30
[52] U.S. Cl. .............................................. 260/429 R
[58] Field of Search ................................... 260/429 R

[56] References Cited

PUBLICATIONS

Chemical Abstracts, 62, 2788c, (1965).
Chemical Abstracts, 65, 12232a, (1966).
Chemical Abstracts, 72, 79181c and 3541z, (1970).
Chemical Abstracts, 76, 46278u, (1972).
Chemical Abstracts 81, 152352b, (1974).
Triplett et al., J. Organometallic Chem., vol. 107, 23–32, (1976).
Lesbre et al., The Organic Compounds of Germanium, John Wiley & Sons, N.Y., pp. 633–645, (1971).
Kumada et al., J. Organometallic Chem. 17, pp. 235–240, (1969).
E. J. Bulten, "Chemistry of Alkyl Polygermanes," State University Utrecht, The Netherlands, 1969, (Doctoral Dissertation).
"Synthesis of Organogermanium Compounds Containing p–Phenylene Group, Some Infrared Characteristics of p–Phenylene Derivatives of Silicon, Germanium, Tin and Lead," Recueil, A. J. Leusink, et al., vol. 83, No. 8, (1964), 844–856.
"Investigations on Organogermanium Compounds IV", Recueil, F. Rijkens, et al., vol. 85, No. 7, (1966), 1223–1229.
"The Preparation of Alkyldigermane Halides", Tetrahedron Letters, E. J. Bulten and J. G. Noltes, No. 29, (1966), 3471–3477.
"Investigations on Organogermanium Compounds," Journal of Organometallic Chemistry, E. J. Bulten et al., vol. 61, (1973), 179–190.
"The Action of Alkali Metals on Phenylgermanium Halides," Journal of American Chemical Society, vol. 82, No. 13, (1960), 3321–3323.

Primary Examiner—Helen M. S. Sneed
Attorney, Agent, or Firm—Brumbaugh, Graves, Donohue & Raymond

[57] ABSTRACT

Germanium compounds, a process for the preparation thereof, a process for the preparation of a medicine using such a germanium compound for the treatment of cancer as well as the shaped medicine thus obtained.

This invention relates to novel germanium compounds, a pharmaceutical composition using the novel compounds and methods for treating cancer using the pharmaceutical composition.

9 Claims, 18 Drawing Figures

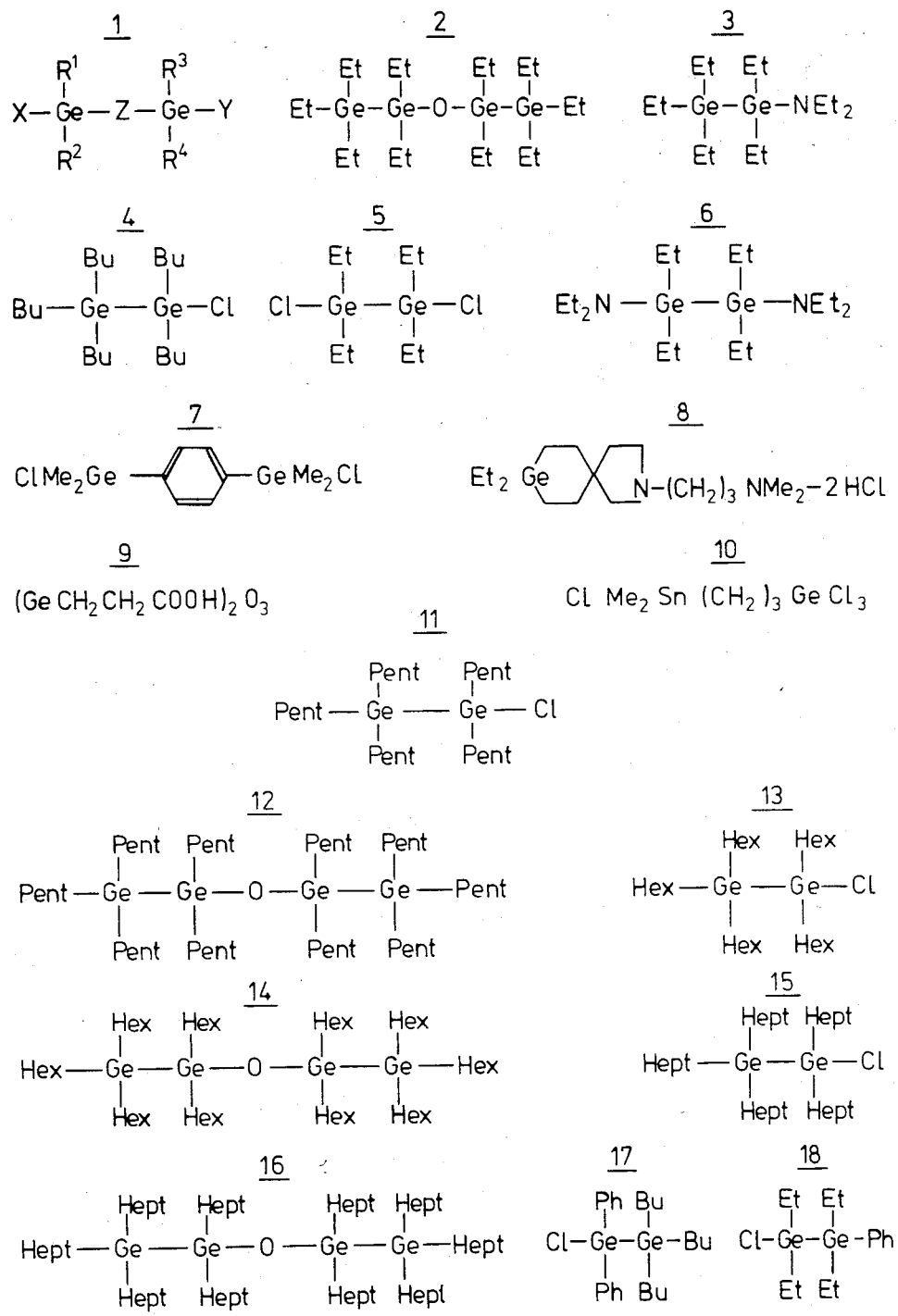

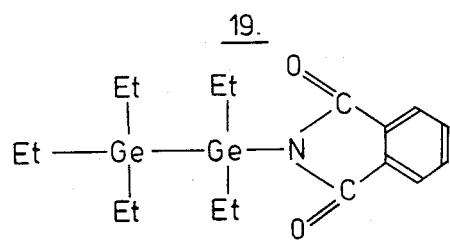
19.
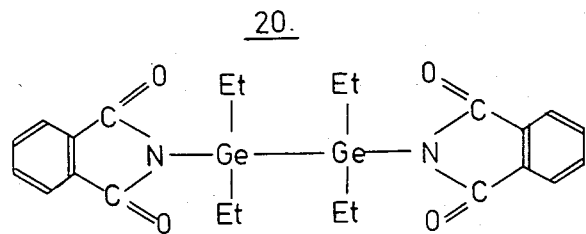
20.
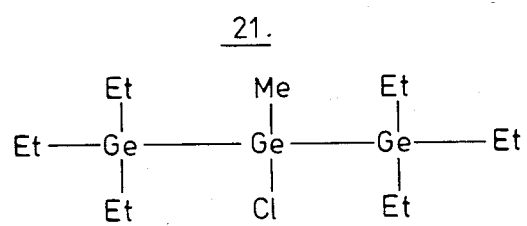
21.
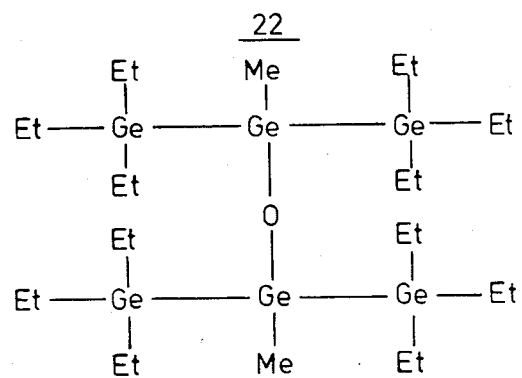
22.
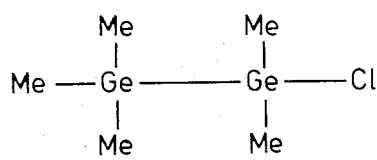
23.

GERMANIUM COMPOUNDS

The invention relates to germanium compounds, to a process for the preparation thereof, to a process for the preparation of a medicine using such a germanium compound for the treatment of cancer, as well as to the shaped medicine thus formed and obtained.

The preparation and application of transition metal complexes is described in Netherlands Patent Application No. 7,904,740, which relates to platinum-diamine complexes. It is stated and elucidated that these platinum-diamine complexes are well suitable for the treatment of cancer, whereas these compounds, in contrast with other well-known platinum compounds, show little or no kidney toxicity.

Very little is known, however, in the field of compounds of main group metals for the present objective.

In Netherlands Patent Application No. 7,212,274 and by C. F. Geschickter and L. M. Rice, a compound haaving formula 8 was described, which at present is being tried clinically.

In Japanese Patent Publication No. 71/02964 a compound is described having formula 9, which has anti-tumor activity.

Now it was found that germanium compounds having formula 1 of the formula sheet wherein $R_1$–$R_4$ represent equal or different, whether or not substituted organic groups, which are bound to germanium via a carbon atom, Y represents a hydrogen atom or an anion group, i.e. an inorganic group or an organic group which is bound to germanium via an electro-negative atom (or heteroatom), X is equal to group Y or to one of the groups $R_1$–$R_4$, and Z is a group —$(CH_2)_n$—, in which n is 0–6, a whether or not substituted aryl group or an organogermyl group having the formula

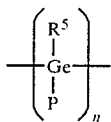

wherein $R^5$ has the same meaning as $R_1$–$R_4$ and P has the same meaning as Y and n is 0–6, are well suitable for the treatment of cancer, while these germanium compounds mostly display little or no kidney toxicity.

Examples of groups $R_1$–$R_4$ are a linear or branched alkyl group, a cycloalkyl group, a whether or not substituted ary group or a whether or not substituted aralkyl group.

Examples of group Y as an inorganic group are a hydrogen atom or an acid radical, such as a halogen atom, a sulphate group, a nitrate group, a phosphate group, a hydroxyl group, or a carbonate group, and as an organic group an alkoxy group, a thioalkyl group, an ester group, a carboxylate group, an imido group like a phthalimidogroup or an amino group —NRR′, in which R and R′ are whether or not equal and represent a hydrogen atom, an alkyl group, an aralkyl group or an aryl group.

The invention, furthermore, relates to the preparation of these compounds, to the preparation of a medicine using a germanium compound as described above, as well as to a shaped medicine thus formed and obtained.

Germanium compounds having the general formula 1 and the preparation of these compounds are known per se from the doctoral dissertation by E. J. Bulten "Chemistry of alkyl polygermanes", State University Utrecht, The Netherlands, 1969. No application of these compounds is stated, however, and certainly not as a medicine for the treatment of cancer.

Among the compounds having formula 1 those having formulae 2–7 and 11–23 are preferred, while the compounds having the formulae 11–20 and 22 are, moreover, new.

An extensive study carried out by the National Cancer Institute, Bethesda, USA, and by the European Organization for Research on the Treatment of Cancer, Brussels, Belgium, has shown that the compounds according to the invention display a high therapeutic activity against cancer.

It is possible to replace one Ge-atom by one Sn-atom. An example of such a compound is indicated by formula 10 and has been incorporated in the following Table.

As will show from this Table, the compounds display interesting anti-tumor activity against, for instance, P 388 lymphocytic leukemia.

TABLE

Anti-tumor activity of germanium compounds against P 388 lymphocytic leukemia in mice, according to "Screening data summary interpretation", US National Cancer Institute, Instruction 14 (1978)

| Compound having the formula of the formula sheet | T/C (%)/Dose (mg/kg)[1] |
|---|---|
| 2 | 141/200–135/100 |
| 3 | 118/100–135/50 |
| 4 | 135/50 |
| 5 | 127/12.5–120/6.25 |
| 6 | 138/50–125/25 |
| 7 | 137/25 |
| 10 | 133/6.25–138/3.12 |
| 23 | 122/16 |

[1]T/C is the ratio survival time (in days) of treated and untreated mice; according to the above-mentioned "Screening data summary interpretation" a compound is considered to be active at T/C values higher than 120%.

The invention is further elucidated by means of the following examples.

The compounds are prepared according to the method described in the above-mentioned doctoral dissertation by E. J. Bulten.

EXAMPLE I

Oxybis(pentaethyldigermane) having formula 2 of the formula sheet. A mixture of 6 g (18.4 mmoles) of chloropentaethyldigermane, 1.6 g (40 mmoles) of sodium hydroxide and 3.5 ml of water was refluxed for 2.5 hours. Extraction with petroleum ether (40°–60° C.) followed by distillation yielded 3.8 g of oxybis(pentaethyldigermane); boiling point 162°–165° C./0.3 mm Hg, $h_D{}^{20}=1.5185$.

Analysis: Calcd. (% by weight): C, 40.23; H, 8.44; Found (% by weight): C, 40.4; H, 8.3.

EXAMPLE II (Diethylamino)pentaethyldigermane having formula 3 of the formula sheet.

A suspension of diethylamine lithium in hexane (24 ml, 24.0 mmoles) prepared from a solution of butyl lithium in hexane and diethylamine, was, under a nitrogen atmosphere, slowly added to a solution of 6.5 g (20.0 mmoles) of chloropentaethyl digermane in 10 ml of hexane. After stirring for 8 hours at ambient temperature, the mixture was filtered under nitrogen. The filtrate was freed from solvent by distillation under atmospheric pressure. The residue obtained was fractionated under reduced pressure, 3.6 g of (diethylamino)pentaethyldigermane being obtained; boiling point 85°–86° C./0.1 mm Hg; $n_D^{20} = 1.5022$.

Analysis: Calcd. (% by weight): C, 46.37; H, 9.73; N, 3.86; Found (% by weight): C, 46.6; H, 9.8; N, 4.0.

EXAMPLE III

Chloropentabutyldigermane having formula 4 of the formula sheet. A mixture of 5.8 g (27.0 mmoles) of germanium tetrachloride and 12.2 g (27.0 mmoles) of hexabutyldigermane was heated for 6.5 hours at 200° C. in a Carius tube. Fractionated distillation yielded 6.0 g of butyltrichlorogermane and 11.2 g of chloropentabutyldigermane; boiling point 130°–131° C./0.06 mm Hg; $n_D^{20} = 1.4932$.

Anaysis: Calcd. (% by weight): C, 51.52; H, 9.73; Cl, 7.61; Found (% by weight): C, 51.5; H, 9.6; Cl, 7.8.

EXAMPLE IV 1,2-Dichlorotetraethyldigermane having formula 5 of the formula sheet.

A mixture of 5.7 g (17.9 mmoles) of hexaethyldigermane and 9.9 g (38.0 mmoles) of tintetrachloride was heated for 6 hours at 180° C. in a Carius tube. Fractionated distillation yielded 5.1 g of pure 1,2-dichlorotetraethyldigermane; boiling point 130°–132° C./16 mm Hg; $n_D^{20} = 1.5197$.

Analysis: Calcd. (% by weight): C, 28.91; H, 6.07; Cl, 21.34; Found (% by weight): C, 29.0; H, 6.1; Cl, 21.2.

EXAMPLE V 1,2-Bis(diethylamino)tetraethyldigermane having formula 6 of the formula sheet.

At −10° C., 41 ml of a 1.7N solution of butyllithium in hexane (70 mmoles) were added to a solution of 5.5 g (75 mmoles) of diethylamine in 25 ml of diethyl ether. After the mixture has been stirred for another half hour, the solution of lithium diethyl amine thus obtained was, under nitrogen and at −20° C., slowly added to a solution of 9.9 g (30 mmoles) of 1,2-dichlorotetraethyldigermane. After having been stirred at ambient temperature for another 3 hours, the reaction mixture was filtered under nitrogen and concentrated by distillation. Fractionated distillation yielded 8 g of 1,2-bis-(diethylamino)tetraethyldigermane; boiling point 92°–94° C./0.04 mm Hg; $n_D^{20} = 1.5045$.

Analysis: Calcd. (% by weight): C, 48.37; H, 9.94; N, 6.90; Found (% by weight): C, 48.4; H, 10.0; N, 7.2.

EXAMPLE VI p-Bis(dimethylchlorogermyl)benzene having formula 7 of the formula sheet.

In a period of half an hour 15.8 g (0.067 moles) of p-dibromobenzene were added dropwise to a suspension of 4.86 g of magnesium in 80 ml of tetrahydrofuran. After refluxing for further 6 hours the mixture was filtered. The filtrate was added dropwise in two hours to a solution of 34.7 g of dimethylgermanium dichloride in 90 ml of tetrahydrofuran. After boiling for further 2 hours, the reaction mixture was evaporated to dryness, wherein 7.3 g of residue were obtained. This residue was extracted three times with 50 ml of boiling benzene. Evaporating the benzene yielded 30 g of a crude product. This was extracted three times with 50 ml of boiling petroleum ether (60°–80° C.). Evaporation yielded 9.8 g of crude product having a melting point of about 122° C. Recrystallization from petroleum ether (60°–80° C.) yielded 5 g of p-bis(dimethylchlorogermyl)benzene; melting point 94°–98° C.

Analysis: Calcd. (% by weight): C, 34.09; H, 4.58; Cl, 20.13; Found (% by weight): C, 34.2; H, 4.3; Cl, 20.2.

EXAMPLE VII

Chloropentapentyldigermane having formula 11 of the formula sheet. A mixture of 6.0 g of hexapentyl digermane, 2.97 g of tin tetrachloride and 25 ml of nitromethane was refluxed under exclusion of moisture during 16 hours.

The resulting two liquid layer system was separated. The under layer was extracted three times each with 75 ml of pentane. The combined upper layer and pentane extracts were extracted once with 50 ml of 4N hydrochloric acid and subsequently once with 50 ml of water. After drying over magnesium sulphate the solvent pentane was removed under reduced pressure, wherein 5.1 g (90%) clear colorless chloropentapentyldigermane were obtained; $n_D^{20} = 1.4875$.

By means of gas chromatography it was determined that the compound was more than 96% pure.

Analysis: Calcd. (% by weight): C, 55.99; H, 10.34; Cl, 6.61; Found (% by weight): C, 55.7; H, 10.3; Cl, 6.9.

EXAMPLE VIII

Oxybis-(pentapenthyldigermane) having formula 12 of the formula sheet.

This compound was prepared according to the process described in Example I starting from 2.0 g of chloropentapentyl digermane, 0.3 g of sodium hydroxide and 2 ml of water.

After removal of the solvent under reduced pressure 1.3 g (51%) of pure oxybis-(pentapentyldigermane) were obtained; $n_D^{20} = 1.4860$.

Analysis: Calcd. (% by weight): C, 59.00; H, 10.89; Found (% by weight): C, 58.8; H, 10.7.

EXAMPLE IX

Chloropentahexyldigermane having formula 13 of the formula sheet. This compound was prepared according to the process described in Example VII, starting from 3.28 g of hexahexyl digermane, 1.31 g of tin tetrachloride and 7 ml of nitromethane.

1.6 g (53%) of colorless liquid chloropentahexyldigermane were obtained; $n_D^{20} = 1.4843$.

Analysis: Calcd. (% by weight): C, 59.41; H, 10.80; Found (% by weight): C, 59.0; H, 10.8.

EXAMPLE X

Oxybis(pentahexyldigermane) having formula 14 of the formula sheet. This compound was prepared according to the process described in Example I, starting from 1.0 g of chloropentaheptyl digermane, 0.6 g of sodium hydroxide and 5 ml of water.

After removal of the solvent under reduced pressure 0.86 g (92%) of oxybis-(pentahexyldigermane) were obtained; $n_D^{20} = 1.4840$.

Analysis: Calcd. (% by weight): C, 62.23; H, 11.32; Found (% by weight): C, 62.0; H, 10.6.

EXAMPLE XI

Chloropentaheptyldigermane having formula 15 of the formula sheet. This compound was prepared according to the process described in Example VII, starting from 3.7 g of hexaheptyl digermane, 1.31 g of tin tetrachloride and 7 ml of nitromethane.

1.7 g (50%) of colorless liquid chloropentaheptyldigermane were obtained; $n_D^{20}=1.4792$.

Analysis: Calcd. (% by weight): C, 62.13; H, 11.17; Found (% by weight): C, 61.9; H, 11.2.

EXAMPLE XII

Oxybis(pentaheptyldigermane) having the formula 16 of the formula sheet.

This compound was prepared according to the process described in example I, starting from 1.0 g of chloropentaheptyldigermane, 0.6 g of sodium hydroxide and 5 ml of water.

After removal of the solvent under reduced pressure 0.80 g (84%) oxybis(pentaheptyldigermane) were obtained; $n_D^{20}=1.4787$.

Analysis: Calcd. (% by weight): C, 64.76; H, 11.64; Found (% by weight): C, 64.0; H, 11.5.

EXAMPLE XIII

1-Chloro-1,1-diphenyltributyldigermane having formula 17 of the formula sheet.

This compound was prepared according to the process described in example VII, starting from 0.7 g of tributyltriphenyldigermane, 0.3 g of tin tetrachloride and 3 ml of nitromethane.

0.4 g (62%) colorless liquid 1-chloro-1,1-diphenyltributyldigermane were obtained.

$^1$H-NMR in CCl$_4$ (Varian-T 60). Measured against TMS. C$_6$H$_5$-Ge: 7.2–7.4 ppm (multiplet), Bu-Ge: 0.5–1.6 ppm (multiplet), Integral ratio H$_{phenyl}$/H$_{butyl}$:- calcd. 10/27; found 10/29.

EXAMPLE XIV

1-Chloro-2-phenyl-tetraethyldigermane having formula 18 of the formula sheet.

To a solution of 9.0 g of 1,2-dichlorotetraethyldigermane in 100 ml of dry diethyl ether 19.2 ml of a 1.4N solution of phenyl magnesium bromide in diethylether were added under exclusion of moisture. After refluxing during 1 hour the reaction mixture was hydrolyzed by addition of a mixture of 25 ml of H$_2$O and 25 ml of saturated ammonium chloride solution.

After extraction with diethyl ether and drying over magnesium sulphate the solution was filtered. The solvent was removed under reduced pressure, wherein a light yellow clear liquid, 8 g (80%) was obtained; $n_D^{20}=1.5534$.

$^1$H-NMR in CCl$_4$ (Varian-T 60). Measured against TMS. H$_{aromatic}$: 7.3 ppm (multiplet), H$_{aliphatic}$: 1.2 ppm (multiplet), Integral ratio: calcd. 5/20; found 5/20.

Analysis: Calcd. (% by weight): C, 44.96; H, 6.74; Cl, 9.48; Found (% by weight): C, 44.8; H, 6.6; Cl, 9.8.

EXAMPLE XV

Pentaethyldigermane-N-phthalimide having formula 19 of the formula sheet.

Under exclusion of moist a mixture of 3.26 g of chloropentaethyldigermane, 2.40 g of potassium phthalimide and 25 ml of dry toluene was refluxed during 6 hours. The resulting mixture was filtered under exclusion of moisture by means of a glass filter and the filtrate was concentrated under reduced pressure. Distillation of the residue under reduced pressure yielded 3.35 g (77%) of pure pentaethyldigermane-N-phthalimide, a colorless liquid; $n_D^{20}$: 1.5632; boiling point 218°–220° C./0.35 mm Hg.

Analysis: Calcd. (% by weight): C, 49.52; H, 6.69; N, 3.21; Found (% by weight): C, 49.2; H, 6.8; N, 3.2.

EXAMPLE XVI

N,N-bisphthalimidotetraethyldigermane having formula 20 of the formula sheet.

This compound was prepared according to the process described in Example XV, starting from 6.0 g of 1,2-dichlorotetraethyldigermane, 7.3 g of potassium phthalimide and 50 ml of dry toluene. 9 g (91%) of pure, white, crystalline N,N-bisphthalimidotetraethyldigermane were obtained; melting point 170°–171° C.

$^1$H-NMR spectrum in CCl$_4$ (Varian-T 60). Measured against TMS. H$_{aromatic}$: 7.73 ppm (symmetrical multiplet), H$_{aliphatic}$: 1.1–1.8 ppm (multiplet), H$_{aromatic}$/H$_{aliphatic}$: calcd. 8/20; found 8/21.

Analysis: Calcd. (% by weight): C, 52.06; H, 5.10; H, 5.06; Found: C, 51.8; H, 5.1; N, 5.0.

EXAMPLE XVII

2-Chloro-2-methylhexaethyltrigermane having formula 21 of the formula sheet.

This compound was prepared according to the process described in Example VII, with the understanding that the reaction was carried out at ambient temperature, starting from 6.0 g of 2,2-dimethylhexaethyltrigermane, 3.53 g of tin tetrachloride and 35 ml of nitromethane.

5.15 g (86%) of pure 2-chloro-2-methylhexaethyltrigermane were obtained; $n_D^{20}=1.5340$.

$^1$H-NMR in CCl$_4$ (Varian-T 60). Measured against TMS. CH$_3$-Ge: 0.9 ppm (singlet), C$_2$H$_5$-Ge: 1.2 ppm (multiplet).

Analysis: Calcd. (% by weight): C, 35.30; H, 7.52; Cl, 8.01; Found (% by weight): C, 35.3; H, 7.6; Cl, 7.7.

EXAMPLE XVIII

Oxybis(1,1,1,3,3,3-hexaethylmethyltrigermane) having formula 22 of the formula sheet.

This compound was prepared according to the process described in Example I, starting from 3.0 g of 2-chloro-2-methylhexaethyltrigermane, 0.6 g of sodium hydroxide and 3 ml of water. 3.1 g (55%) of colorless, liquid oxybis(1,1,1,3,3,3-hexaethylmethyltrigermane) were obtained; $n_D^{20}=1.5410$.

$^1$H-NMR in CCl$_4$ (Varian-T 60). Measured against TMS. Me-Ge: 0.67 ppm (singlet), Et-Ge: 1.1 ppm (multiplet).

Analysis: Calcd. (% by weight): C, 37.61; H, 8.01; Found (% by weight): C, 37.3; H, 8.1.

EXAMPLE XIX

Chloro-pentamethyldigermane having formula 23 of the formula sheet.

This compound was prepared according to the process described in Example VII, starting from 5.9 g of hexamethyldigermane, 6.7 g of tin tetrachloride and 30 ml of nitromethane. The yield was 2.8 g (44%); boiling point 64°–66° C.; $n_D^{20}=1.4919$.

We claim:

1. A germanium compound having the formula:

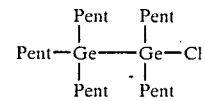

2. A germanium compound having the formula:

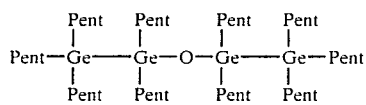
3. A germanium compound having the formula:
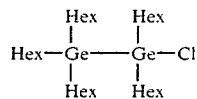
4. A germanium compound having the formula:
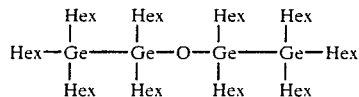
5. A germanium compound having the formula:
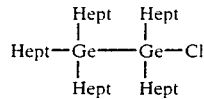
6. A germanium compound having the formula:
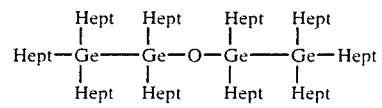
7. A germanium compound having the formula:
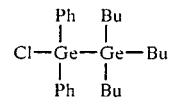
8. A germanium compound having the formula:
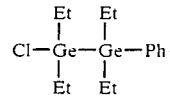
9. A germanium compound having the formula:
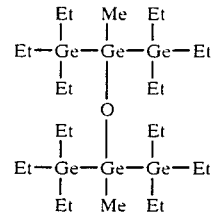
* * * * *